United States Patent [19]

Eberle

[11] 4,364,904

[45] Dec. 21, 1982

[54] TWO PART STAND WITH RECEPTACLES FOR TEST TUBES

[76] Inventor: Günter Eberle, Gartenstrasse 100,, 7200 Tuttlingen, Fed. Rep. of Germany

[21] Appl. No.: 945,217

[22] Filed: Sep. 25, 1978

[30] Foreign Application Priority Data

Sep. 27, 1977 [DE] Fed. Rep. of Germany ....... 2743433

[51] Int. Cl.$^3$ .............................................. B01L 9/06
[52] U.S. Cl. ...................................... 422/104; 211/74
[58] Field of Search .......................... 422/104; 211/74; 233/26

[56] References Cited

U.S. PATENT DOCUMENTS

| | | | |
|---|---|---|---|
| 3,533,453 | 10/1970 | Pastfach | 422/100 X |
| 3,674,198 | 7/1972 | Eberle | 211/74 X |
| 4,032,066 | 6/1977 | Wright | 211/74 X |
| 4,040,234 | 8/1977 | Stockdale et al. | 422/104 X |
| 4,068,798 | 1/1978 | Rohde | 211/74 X |

FOREIGN PATENT DOCUMENTS 1205752 9/1970 United Kingdom .................. 211/74

*Primary Examiner*—Arnold Turk
*Attorney, Agent, or Firm*—William R. Price

[57] ABSTRACT

The invention is shown as a two part stand having receptacles for holding test tubes. The first, top part comprises a plurality of vertical receptacles for receiving the test tubes in a close fitting relationship. The second, bottom part is a rack that is interconnected to the top part in an easily detachable manner, and it comprises a base plate and vertical corner posts so that it is possible to look through all four sides of the bottom part of the stand and observe the contents of the test tubes.

3 Claims, 4 Drawing Figures

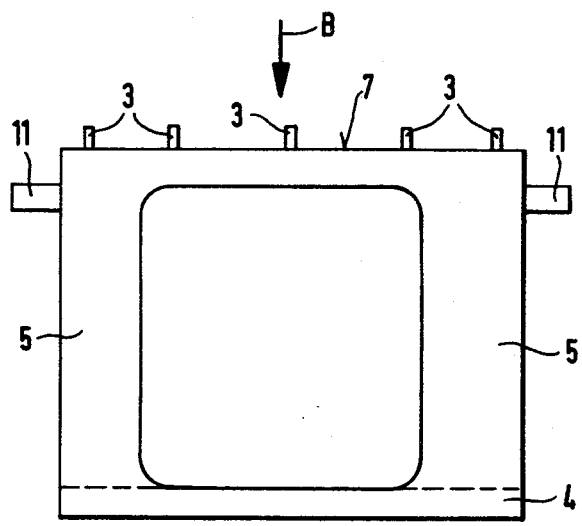
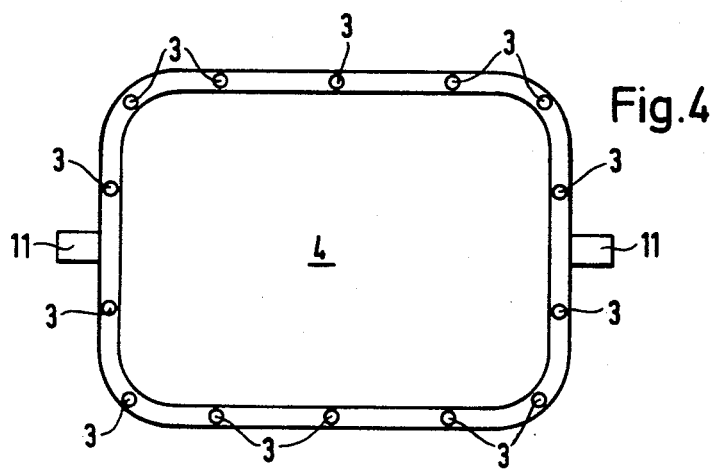

TWO PART STAND WITH RECEPTACLES FOR TEST TUBES

This invention relates to a two-part stand having receptacles for a plurality of test tubes. Such test tube stands are used, e.g., for insertion in centrifugal cups, for analyzing the content of test tubes, for inserting in system boxes or other containers, which accommodate these test tube stands, e.g., in lab stands. They then replace the so called test glass racks.

Up until now test tube stands were fabricated in one piece. They exist in a variety of designs, namely either with bores or openings below for looking through in a horizontal direction, or they have bores for accommodating test glasses of widely varying diameters. There are also various sizes of such tube stands which are, for example, rectangular or square in plan. A disadvantage of prior art stands is that many different test tube stands of this kind must be kept in stock, depending on the respective purpose of use. Known test tube stands also include those where two parts are interconnected, e.g., by means of screws or adhesive bonding, for forming a test tube stand.

OBJECTS OF THE INVENTION

The object of the invention is to provide a two-part test tube stand, where the parting line between these two parts is so arranged that two independently operativeparts are produced.

A further object of the present invention is to provide a two part interconnected test tube stand where the top part has a plurality of test tube receptacles while the bottom part is generally of open rack design for viewing the test tubes from a plurality of directions, and the bottom part includes suspension means adapted for supporting the entire stand directly in a centrifuge without the need of a separate receptacle for supporting the stand in the centrifuge.

To solve this objective, the invention is characterized in that the parting line between both parts extends substantially perpendicular to the longitudinal direction of the vertical receptacles for the test tubes so that a top part and a bottom part are formed, which are interconnected in an easily detachable manner.

On inserting such a stand in a centrifuge, a centrifugal force acts parallel to the longitudinal axis of the receptacles for the test tubes, i.e., in a direction perpendicular to said horizontal parting line. The interconnection between the top part and the bottom part is therefore improved, namely because the stand is attached directly to the centrifuge via the bottom part. The centrifugal force acting on the top part, therefore, acts in a direction toward the bottom part in such a way that both parts are pressed together. On the other hand, both parts can be easily detached by hand from each other and, therefore, inserted separately. For both parts numerous embodiments are feasible.

SUMMARY OF THE INVENTION

The top part has the receptacles for the test tubes, so that, with close fitting dimensions, for one and the same bottom part variously designed top parts can be inserted. This is exemplified by top parts with receptacles of various diameters for variously sized test tubes or the like. Because of the described measures, the keeping of stock is considerably reduced. Also, smaller parts are fabricated, so that the machinery purchase price for fabricating top and bottom parts can be reduced. Preferably both parts are molded from plastics.

The bottom part may be designed as a rack with a base plate and vertical corner posts, so that with a rectangular ground plan of the stand one can look through the bottom part from the four sides and observe the contents of the test tubes. The bottom rack includes a pair of suspension tabs for suspending the two-part stand in a centrifuge. This embodiment requires very little material. Moreover two of the vertical corner posts can be joined at the opposite sides to form stands, so that both material consumption and stability are increased. With this embodiment, looking through the rack is possible in only two directions.

BRIEF DESCRIPTION OF THE DRAWINGS

The invention is explained in more detail below with reference to an exemplified embodiment, from which other important features will be evident.

FIG. 3 is a lateral view of a bottom part fitting the top part according to FIGS. 1 and 2;

FIG. 4 is a top plan view in the direction of arrow B in FIG. 3.

FIGS. 1 and 2 show the top part of a stand, FIGS. 3 and 4 the bottom part of a stand. First the top stand will be described with reference to FIGS. 1 and 2. It is molded from plastics in one piece. Actually it consists of a cubic block, which has vertical receptacles 1 passing through its thickness, into which matchingly dimensioned test tubes can be inserted. Said receptacles are arranged parallel to each other in rows and columns. At the edge of the block several cutouts 2 of smaller diameter are formed, which are blind holes. These cutouts are engaged by pins 3, which are molded onto the topside of the bottom stand (see FIGS. 3 and 4).

Figure 1:
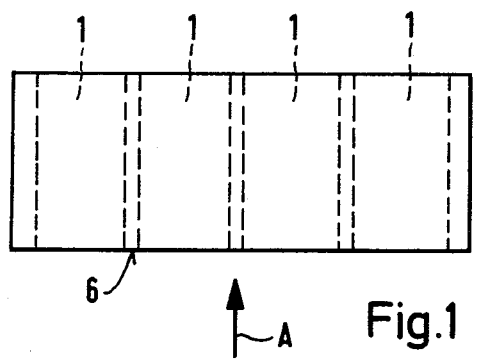
FIG. 1 is a lateral view of the top part of a stand according to the invention.

The cutouts 2 may alternatively be provided at the top side or at both the top and bottom sides of the block according to FIG. 1.

The bottom part of the stand according to FIGS. 3 and 4 consists of a base plate 4 with four vertical corner posts 5, which are interconnected at the top, so that the pins 3 can be molded all around the top edge.

Figure 2:
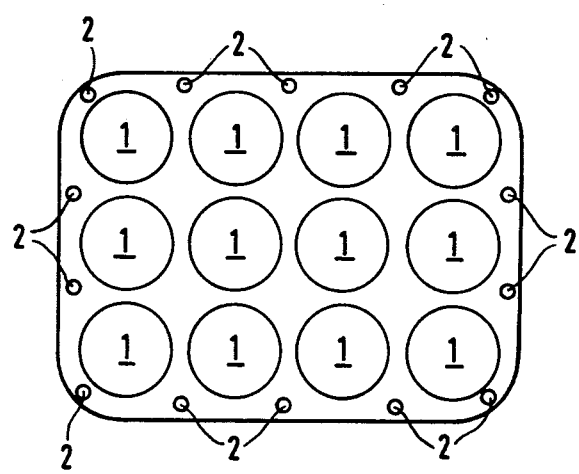
FIG. 2 is a bottom plan view in the direction of arrow A in FIG. 1.

In use, the top part according to FIGS. 1 and 2 is placed on the bottom part according to FIGS. 3 and 4 so that the pins 3 of the bottom part engage in the cutouts 2 of the top part. The horizontal parting line for both parts is formed by the bottom edge 6 of the top block according to FIG. 1 or respectively the top edge 7 of the bottom rack according to FIG. 3.

Preferably the pins 3 are provided on the topside of the bottom part, because then the pins cannot break off.

The top part and bottom part may be in different colors. They may also have different markings e.g., in the shape of tabs. The bottom part may have oppositely directed tabs, as indicated at item 11, for setting it into a centrifuge. Instead of an easily detachable connection by means of pins and cutouts, other connections may be provided, e.g., dovetail-like guides, undercuts or other positive-locking connections, which insure satisfactory seating.

What is claimed is:

1. A two-part stand for receiving test tubes for insertion into a centrifuge, comprising a top part and a bottom part, wherein the top part includes a plurality of vertical test tube receptacles, and the bottom part represents an open rack for receiving test tubes freely therein while permitting viewing of the test tubes, the two parts are separated by a parting line that is substantially perpendicular to the longitudinal direction of the vertical receptacles, easily detachable means for interconnecting the top and bottom parts against horizontal displacement, and the bottom part additionally includes a pair of oppositely-directed tabs whereby the stand may be suspended directly in a centrifuge, without the need for an additional receptacle.

2. A two-part stand as recited in claim 1 wherein the said easily detachable means includes pin members on one part that extend parallel to the longitudinal direction of the vertical receptacles and mating cutouts in the other part for receiving the pin members.

3. A two-part stand as recited in claim 1 wherein the bottom part includes a bottom plate, vertical corner posts and a peripheral top edge (7).

* * * * *